United States Patent
Pelkey

[11] Patent Number: 5,911,711
[45] Date of Patent: Jun. 15, 1999

[54] LUBRICANT SYSTEM FOR HYPODERMIC NEEDLES AND METHOD FOR ITS APPLICATION

[75] Inventor: Brian J. Pelkey, Rockaway, N.J.

[73] Assignee: Becton, Dickinson and Company, Franklin Lakes, N.J.

[21] Appl. No.: 09/106,669

[22] Filed: Jun. 29, 1998

[51] Int. Cl.[6] .................................. A61M 25/00; C08L 83/04
[52] U.S. Cl. .......................... 604/265; 524/731; 424/387
[58] Field of Search ...................................... 604/265, 264, 604/266, 272; 524/862, 730, 731, 588, 858, 86; 528/15, 31, 32; 427/2.12, 452, 387, 388, 2, 409, 435

[56] References Cited

U.S. PATENT DOCUMENTS

| | | | |
|---|---|---|---|
| 3,355,424 | 11/1967 | Brown | 260/46.5 |
| 3,574,673 | 4/1971 | Schweiger | 117/132 |
| 4,461,867 | 7/1984 | Surprenant | 524/788 |
| 4,534,363 | 8/1985 | Gold | 128/772 |
| 4,664,657 | 5/1987 | Williamitis et al. | 604/265 |
| 4,720,521 | 1/1988 | Spielvogel et al. | 524/862 |
| 4,806,430 | 2/1989 | Spielvogel et al. | 604/187 |
| 4,838,876 | 6/1989 | Wong et al. | 604/265 |
| 5,185,003 | 2/1993 | Williamitis et al. | 604/265 |
| 5,213,839 | 5/1993 | Awazu et al. | 427/2 |
| 5,258,013 | 11/1993 | Granger et al. | 606/223 |
| 5,338,312 | 8/1994 | Montgomery | 604/230 |
| 5,352,378 | 10/1994 | Mathisen et al. | 252/54 |
| 5,380,299 | 1/1995 | Fearnot et al. | 604/265 |
| 5,456,948 | 10/1995 | Mathisen et al. | 427/387 |
| 5,458,616 | 10/1995 | Granger et al. | 606/223 |
| 5,536,527 | 7/1996 | Prasad | 427/2.28 |
| 5,536,582 | 7/1996 | Prasad et al. | 428/450 |
| 5,628,826 | 5/1997 | Prasad | 118/232 |
| 5,653,695 | 8/1997 | Hopkins et al. | 604/265 |

FOREIGN PATENT DOCUMENTS 2093585   10/1993   Canada .

*Primary Examiner*—Corrine McDermott
*Assistant Examiner*—Sharon Finkel
*Attorney, Agent, or Firm*—Arthur D. Dawson

[57] ABSTRACT

A lubricated hypodermic needle of the invention includes an elongate tube with an outside surface, a proximal end, a distal end and an open bore therethrough. The needle has a hub attached to the proximal end of the needle that is used to attach the needle to a fluid handling device. The invention includes a lubricious coating applied to and adherent to the outside surface of the tube. The lubricious coating has a first layer formed from an at least partially cured organosiloxane copolymer and polydimethylsiloxane that has a viscosity greater than about 1000 centistokes. The lubricious coating has a second layer, applied as a secondary operation onto the first layer, that includes a polydimethylsiloxane having a viscosity between about 50 centistokes and about 350 centistokes.

8 Claims, 4 Drawing Sheets

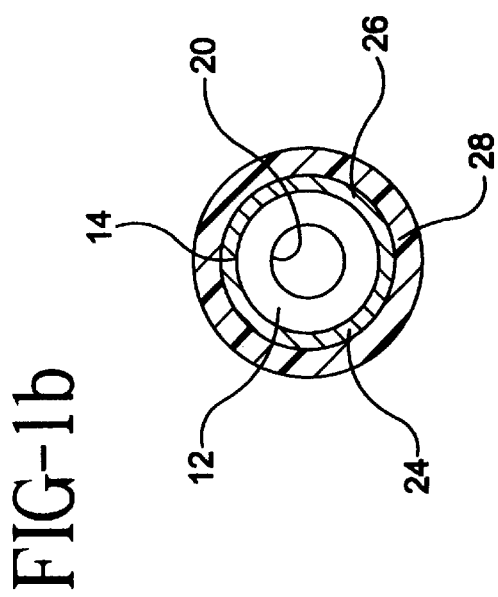
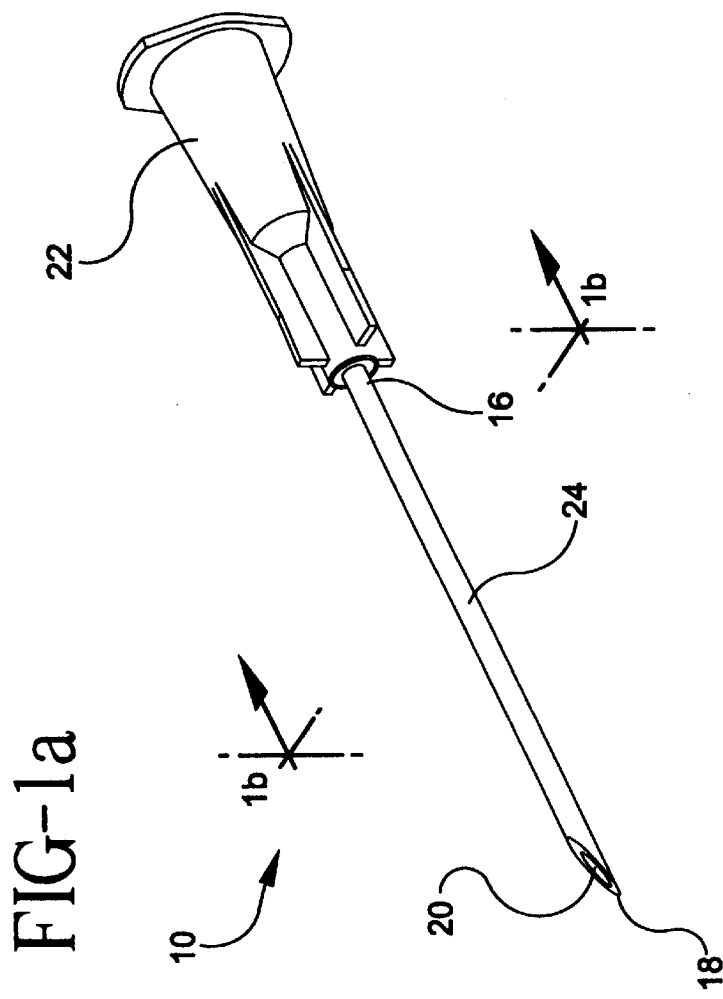

LUBRICANT SYSTEM FOR HYPODERMIC NEEDLES AND METHOD FOR ITS APPLICATION

FIELD OF THE INVENTION

This invention is generally related to hypodermic needles and more particularly to lubricated hypodermic needles and a method for applying the lubricant coating thereto.

BACKGROUND

Hypodermic needles are widely used in delivering and withdrawing fluids in medical practice. As originally used, hypodermic needles were used many times, the needles being sterilized between usages. A practitioner would sharpen the needles when they became dull, and then sterilize them prior to the next usage. Since the needles were reused, and often may have needed sharpening, the presence or absence of any lubrication on the outer surface of the needle had little effect on the penetration force or the pain perceived by the patient who was the recipient of the needle. With the development of commercially manufactured disposable needles that always have a fresh well-sharpened point, there was recognition that lubrication of the needle substantially reduced the pain perceived by the patient when a needle was administered to them.

A convention is followed in this disclosure wherein the portion of a device toward the practitioner is termed proximal and the portion of the device toward the patient is termed distal.

A tissue penetration by a hypodermic needle involves a sequence of events that collectively are perceived by the patient as whether or not the penetration caused pain. A distal point of the needle first touches the skin surface, stretches it, the point then cuts into the surface and begins penetration into the tissue. As the shaft of the needle passes through the original cut and into the tissue, there is also sliding friction of the tissue against the needle surface. In the hypodermic needle art when the forces for performing a hypodermic needle penetration are measured, the force measured prior to the needle point cutting the tissue is termed the "peak penetration force", also called "F2" and the force required to continue the penetration into the tissue is called the "drag force" or "F4". One primary component of the drag force is the sliding friction of the tissue against the surface of the needle shaft. When a subcutaneous or intra-muscular penetration is made with a hypodermic needle, the penetration depth is generally between about 0.5 cm to about 2.5 cm into the patient's tissue. As a result, the practitioner generally does not generally perceive differences in the needle point's penetration of layers. Additionally, most subcutaneous and intra-muscular hypodermic penetrations are made at a relatively high rate (20 cm to 25 cm per second) and utilize the full length of the needle. The rapid penetration rate additionally reduces any perception of layers. The use of lubricant on the surface of hypodermic needles in combination with very well sharpened needles also significantly reduces both the peak penetration force and the drag force. When the reductions by lubrication of the peak penetration force and the drag force of the needle are coupled with the short duration resultant from the high penetration rate, a patient's perception of the painfulness of the penetration is generally significantly reduced. As a result, almost all single-use sterile disposable needles are supplied with a lubricant already applied to substantially the entire needle outside surface.

SUMMARY

A lubricated hypodermic needle of the invention includes an elongate tube with an outside surface, a proximal end, a distal end and an open bore therethrough. The needle has a hub attached to the proximal end of the needle that is used to attach the needle to a fluid handling device. The invention includes a lubricious coating applied to and adherent to the outside surface of the tube. The lubricious coating has a first layer formed from an at least partially cured organosiloxane copolymer and polydimethylsiloxane that has a viscosity greater than about 1000 centistokes. The lubricious coating has a second layer, applied as a secondary operation onto the first layer, that includes a polydimethylsiloxane having a viscosity between about 50 centistokes and about 350 centistokes.

The lubricated needle of the invention with the second layer that includes low viscosity polydimethylsiloxane provides patients who are recipients of these needles with a perceptibly less painful experience than is found with current commercially available needles. The application of a second layer over the first at least partially cured layer is a relatively simple manufacturing process that provides a statistically significant improvement over the currently available products.

BRIEF DESCRIPTION OF THE DRAWINGS

FIG. 1a is a perspective view of the hypodermic needle of the invention;

FIG. 1b is a schematic cross-sectional view of the invention of FIG. 1a taken along the line 1b—1b;

DETAILED DESCRIPTION

Figure 2:
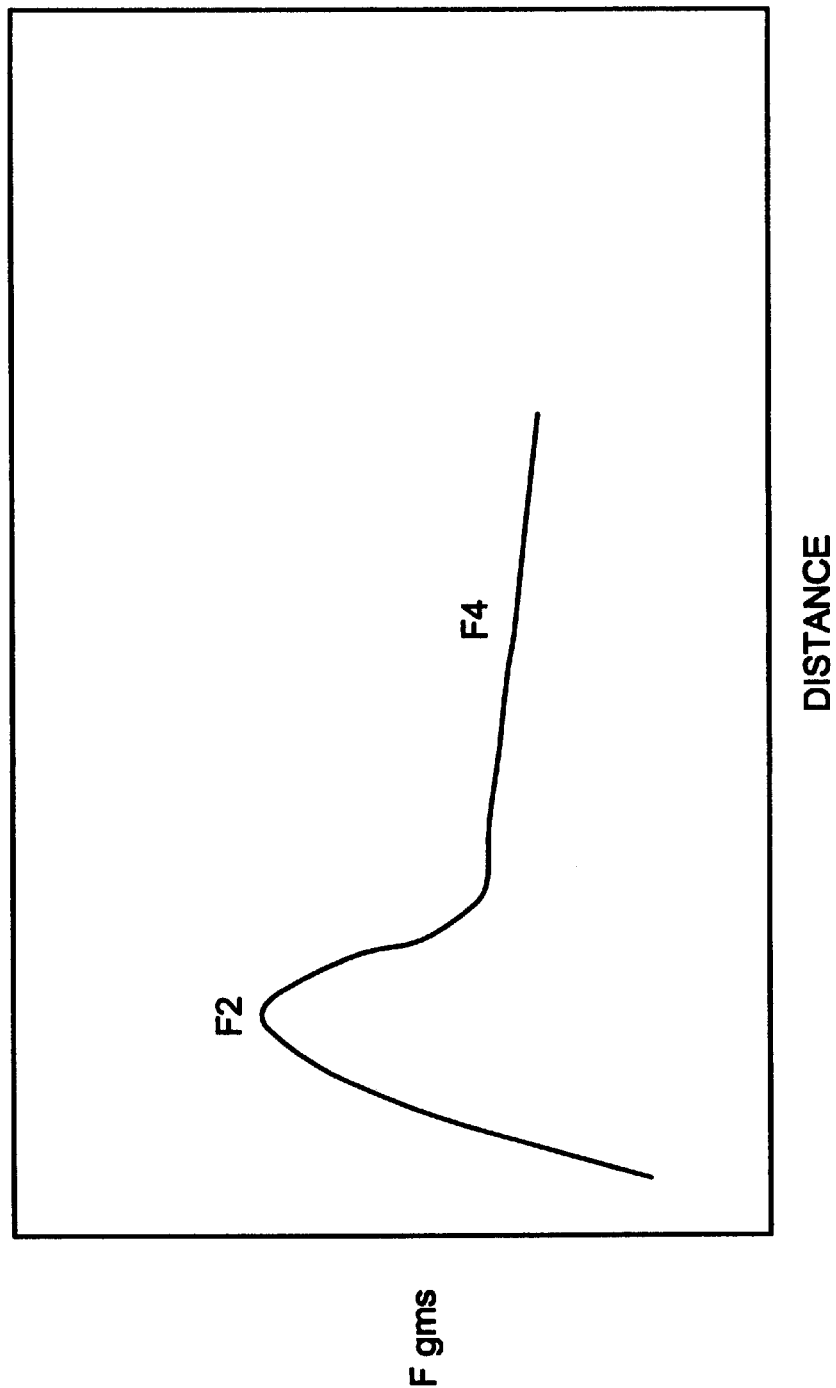
FIG. 2 is a graphical representation of the penetration force measured during a penetration of a hypodermic needle into a rubber vial stopper.

While this invention is satisfied by embodiments in many different forms, there is described in the examples and is herein described in detail, a preferred embodiment of the invention with the understanding that the present disclosure is to be considered exemplary of the principles of the invention and is not considered to limit the invention to the embodiments exemplified. The scope of the invention is measured by the appended claims and their equivalents. A convention followed in this disclosure describes as "distal" the portion of the needle toward the patient and away from the practitioner while "proximal" is that portion of the needle toward the practitioner and away from the patient.

Referring to FIGS. 1a and 1b, a lubricated hypodermic needle 10 of the invention includes an elongate tube 12 with an outside surface 14, a proximal end 16, a distal end 18 and an open bore 20 therethrough. Needle 10 has a hub 22 attached to proximal end 16 of the needle that is used to attach needle 10 to a fluid handling device. The invention includes a lubricious coating 24 applied to and adherent to outside surface 14 of the tube. Lubricious coating 24 has a first layer 26 formed from an at least partially cured organosiloxane copolymer and polydimethylsiloxane that has a viscosity greater than about 1000 centistokes. The lubricious coating has a second layer 28, applied as a secondary operation onto first layer 26, that includes a polydimethylsiloxane having a viscosity between about 50 centistokes and about 350 centistokes. Preferably, distal end 18 is formed into a sharpened point.

As an alternate to hub 22 being fixedly attached to needle 10, the needle of the invention may be fixedly attached directly to a fluid handling device such as a syringe. Additionally, lubricated needles of the invention are also useful for punctures to blood vessels. Needles of the invention may be beneficially incorporated into devices for these types or other applications and be considered within the scope of the invention.

A preferred method for lubricating needle 10 of the invention includes preparing a curable coating mixture comprising about four parts of a mixture of {50% solids (w/w)} dimethyl cyclosiloxane and dimethoxysilyldimethylaminopropyl silicone polymer in a mixture of mineral spirits and isopropyl alcohol (available from Dow-Corning, Midland, MI, as MDX 4-4159 fluid) and about two parts of polydimethylsiloxane (12,500 centistoke viscosity, available as DC-360 from Dow-Corning, Midland, Mich.) in about ninety four parts of a fugitive solvent, preferably HCFC-141b (Allied Signal, Morristown, N.J., as Genesolve 2000) or other substantially nonpolar volatile and inert solvent. Applying the coating mixture to the outside surface of the needle by dipping the needle into the curable coating mixture at ambient temperature, preferably mounted on a rack and dipped into the mixture in a point down orientation, at a rate about four centimeters per second. The needle is allowed to remain resident in the curable mixture for about ten seconds, then withdrawn from the coating mixture at a rate about four centimeters per second and re-oriented to a tip upward position. Preferably, compressed air is then applied to hub 22 to ensure that bore 20 is clear of lubricant. Needles 10 having first layer 26 thereon are then stored in the point up orientation to allow first layer 26 to at least partially cure.

The term "partially cured copolymer" as used in this description is defined as a crosslinked or partially crosslinked copolymer which has insoluble, infusible coherent three-dimensional structure within which an unstructured or partially cured fluid copolymer is contained. The cured or partially cured copolymer of the first layer is relatively soft and waxy as contrasted to hard vitreous resins which may develop fractures.

The soft and waxy nature of the first layer material is further facilitated by the inclusion of polydimethylsiloxane with a viscosity greater than about 1000 centistokes. Preferably, the polydimethylsiloxane used in the first layer has a viscosity about 12,500 centistokes. The cure may be allowed to occur at ambient conditions, but the rate of the cure may be accelerated by oven warming at temperature above ambient but less than about 100° C., preferably about 82° C. until the coating is sufficiently cured. Higher temperatures may also be used to accelerate the cure of first layer 26, but in cases where hub 22 is formed from a thermoplastic, temperatures below about 100° C. are preferred. Following the cure of first layer 24, the method further includes applying a second layer 28 of a polydimethylsiloxane that has a viscosity between about 50 centistokes and about 350 centistokes viscosity. Suitable polydimethyl siloxanes are available from DowCorning, Midland, Mich., and United Chemical Technologies, Bristol, Pa. Preferably, second layer 28 is applied over cured first layer 26 by dipping needle 10 in a mixture of the polydimethyl siloxane in a fugitive solvent. Preferably, needle 10 is dipped in a mixture of the polydimethyl siloxane of about 3 parts in about 97 parts of HCFC-141b solvent or other substantially nonpolar volatile and inert solvent (w/w) at ambient conditions.

The dipping process is preferably performed with needle 10 in a point down orientation at a rate of four centimeters per second. Needle 10 is allowed a sufficient residence time in the coating mixture, preferably about ten seconds, to acquire a coating of the material and then withdrawn from the coating mixture at a rate of about four centimeters per second. The needle is then preferably re-oriented to a tip up position and allowed sufficient time for the solvent to evaporate. For the purpose of this study, the coatings were applied by dipping the needles into solutions of the coating materials. One skilled in the art of applying coatings to objects should recognize that most other methods of applying coatings to objects including, but not limited to, spraying as a dilute solution, spraying as a "neat" liquid, cascade-type application of either a dilute solution or a neat liquid, application from absorbent pads and the like are also applicable and are considered as part of method of the invention.

Figure 3:
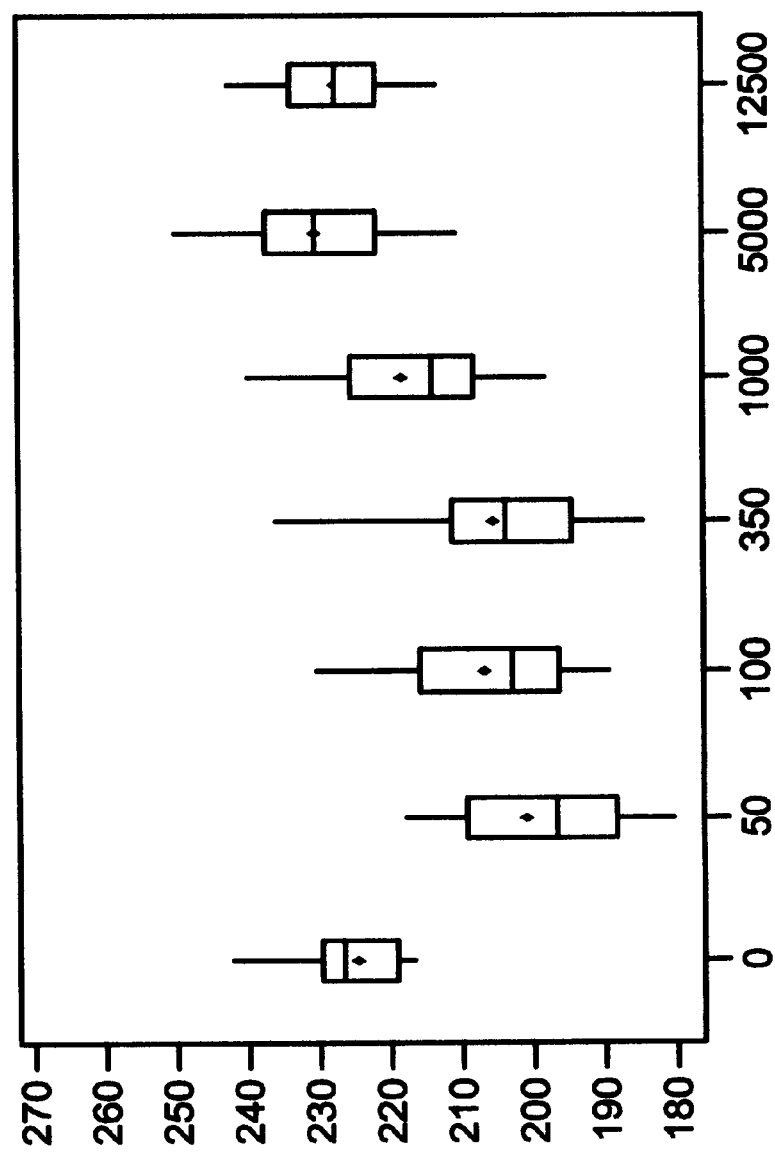
FIG. 3 is a graphical comparison of the peak penetration forces determined for a series of hypodermic needles introduced into a rubber vial stopper.
Figure 4:
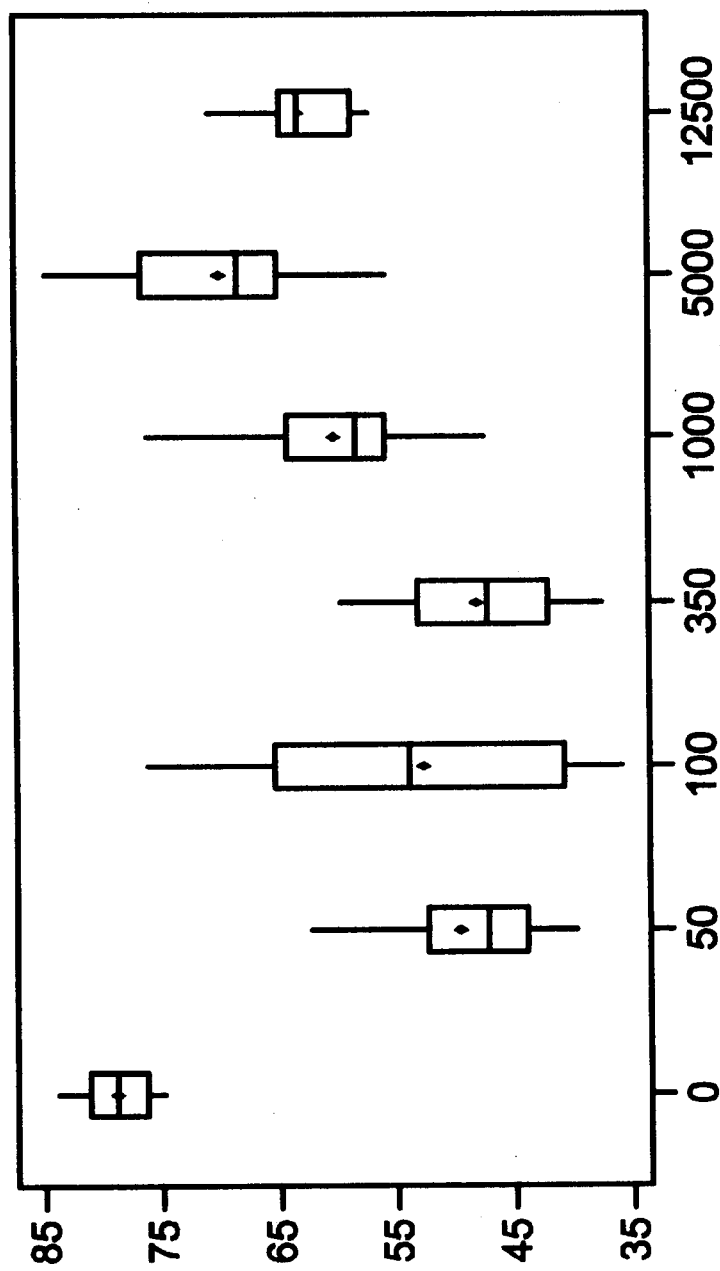
FIG. 4 is a graphical comparison of the drag forces determined for a series of hypodermic needles introduced into a rubber vial stopper.

Referring now to FIGS. 2, 3 and 4, a series of groups of needles 10 (n=20 for each example condition) with lubricious coating 24 as described above was prepared for a needle penetration force study. The several test groups were identically coated with first layer 26 as described above. The composition of second layer 28 was varied as follows:

| Sample | Coating Composition |
|---|---|
| Control | First layer 26 only |
| 50 centistoke polydimethylsiloxane | 3 parts siloxane in 97 parts HCFC-141b |
| 100 centistoke polydimethylsiloxane | 3 parts siloxane in 97 parts HCFC-141b |
| 350 centistoke polydimethylsiloxane | 3 parts siloxane in 97 parts HCFC-141b |
| 1000 centistoke polydimethylsiloxane | 3 parts siloxane in 97 parts HCFC-141b |
| 5000 centistoke polydimethylsiloxane | 3 parts siloxane in 97 parts HCFC-141b |
| 12,500 centistoke polydimethylsiloxane | 3 parts siloxane in 97 parts HCFC-141b |

Referring now to FIG. 2, a graphical representation of a needle penetration into a substrate is shown. In the testing conducted for this comparison, each needle being tested for penetration properties is driven substantially vertically downward into a standard commercial vial stopper at a substantially constant rate of about 1.25 centimeters per second using an instrument with the needle being tested affixed to a calibrated load cell. The "y" axis denotes the resistance force in grams as the needle is advanced into the stopper by the instrument. The "x" axis is representative of the distance of the penetration. All of the needles used for the purpose of this example are 22 gauge and about 3.8 centimeters long, however, the lubrication and method of application of the invention is applicable to and includes other sizes of needles that may be required in any procedure where a lubricated needle is beneficial. The graph shown in FIG. 2 begins as distal point 18 touches the substrate (i.e. the patient's skin or in this case a rubber stopper), stretches the substrate and shows an increasing resistance force until distal point 18 begins to cut the substrate. This peak penetration force is termed "F2". As soon as the point begins to cut the substrate, the recorded force decreases until the elongate tube is introduced through the cut initiated by the point. Once only the tube is moving through the cut, the observed force is termed the drag force or "F4". Lubrication of a hypodermic needle reduces both the F2 and F4 forces dramatically.

In the present examples, the control is an identical needle lubricated only with the curable first layer lubrication. These control needles show a mean peak penetration force of about 224 grams. This first layer lubrication system, used here as a control, is representative of most commercially available disposable needles. A similar unlubricated or "dry" needle with a similar substrate would show a peak penetration force (F2) of about 900 to about 1,000 grams. Thus, the standard commercial lubrication system is effective at significantly reducing peak penetration forces when compared to the peak penetration force seen with a "dry" needle. The same effect of the standard first layer lubrication system is seen with drag forces (F4). The mean drag force seen with the control needle is about 78 grams. Again, a similar "dry" unlubricated needle exhibits drag forces at least one order of magnitude higher than the forces seen with the standard first layer of lubrication. These reductions of the peak penetration and drag forces of the lubricated needles when compared to identical dry unlubricated needles are coupled with substantial reductions in perceived pain by the recipients of the needles and by practitioners administering the needles.

In this study, standard halobutyl rubber 20 mm snap plug vial stoppers, supplied by Abbott Labs, (formulation #5153, Shore A durometer 46, Specific gravity 1.18, compression set 15%) were used as the penetration substrate. It is expected that similar results would be seen with other commonly used substrates, such as preserved pigskin and other commonly used elastomeric materials. Pain perception and user perception data were collected using human volunteer participants in an IRB reviewed test protocol that included both 22 gauge needles similar to those reported in this description and with 27 gauge needles prepared under similar conditions to those described here for the 22 gauge needles.

Referring now to FIG. 3, box and whisker diagrams are used to illustrate the peak penetration forces (F2) seen for the several experimental needle groups. The results show that the addition of second layer 28 lubrication in the case where the polydimethylsiloxane component of the second layer coating solution is either 50, 100 or 350 centistokes viscosity, the peak penetration force is reduced to about 50 grams, 53 grams and 47 grams respectively compared with the 224 grams seen with the control. This reduction in peak penetration force is both statistically significant and perceptible both by a skilled practitioner performing a needle penetration and by a recipient of such a penetration.

FIG. 4 again uses box and whisker diagrams to compare the drag forces (F4) seen for the several experimental needle groups. The results show that the addition of second layer 28 in the case where the polydimethylsiloxane component of the second layer coating solution is either 50, 100 or 350 centistokes viscosity, the mean drag force is about 50, 52 and 48 grams respectively. This is compared to the 78 gram drag force seen with the control. Again, this reduction in drag force is perceptible by both the recipient of the needle and by the practitioner administering the needle to the patient.

Hypodermic needles prepared according to the present invention provide medical practitioners with both a user and recipient perceptible improvement over standard commercially available hypodermic needles in administering medicaments and drawing blood samples by reducing the perceived pain caused by the needle penetration.

What is claimed is:

1. A lubricated hypodermic elongate tube needle comprising:

an elongate tube having an outside surface, a proximal end, a distal end and an open bore therethrough;

a hub attached to said proximal end of said elongate tube for attaching said elongatic tube to a fluid handling device;

a lubricious coating applied to and adherent to said outside surface of said elongate tube comprising a first layer formed from an at least partially cured organosiloxane copolymer and polydimethylsiloxane having a viscosity greater than about 1000 centistokes and a second layer, applied as a secondary operation onto said at least partially cured first layer, including a polydimethylsiloxane having a viscosity between about 50 centistokes and about 350 centistokes.

2. The hypodermic needle of claim 1 wherein said partially cured organosiloxane copolymer of said first layer further comprises about fifty percent (w/w) dimethyl cyclosiloxane and dimethoxysilyldimethylaminoethylaminopropyl silcone polymer.

3. The hypodermic needle of claim 1 wherein said first layer of said lubricious coating further comprises a ratio of said at least partially cured organosiloxane copolymer to said polydimethylsiloxane of about two parts (w/w) of said at least partially cured organosiloxane copolymer to about one part (w/w) of polydimethylsiloxane having a viscosity about 12,500 centistokes.

4. A method for lubricating hypodermic needles comprising:

applying a coating of a first material comprising an organosilane copolymer including a polydimethylsiloxane having a viscosity greater than about 1000 centistokes to an outside surface of a hypodermic needle;

allowing said first material to at least partially cure; and applying, as a secondary operation, a coating of a second material comprising a polydimethylsiloxane having a viscosity between about 50 centistokes and about 350 centistokes onto said at least partially cured first layer.

5. The method of claim 4 wherein said first applying step further comprises applying said polydimethyl siloxane of said first layer coating material having a viscosity of about 12,500 centistokes.

6. The method of claim 4 wherein each of said applying steps for said first material and said second material further each comprises dipping said needles in a solution of each of said materials comprising a fugitive solvent.

7. The method of claim 6 wherein said dipping of said needles in each said solutions of each of said materials comprising a fugitive solvent further comprises selecting HCFC-141*b* as said fugitive solvent and and preparing said solutions by mixing said first material at a concentration of about six parts of said first material in about ninety-four parts HCFC-141*b* and mixing said second material at a concentration of about three parts of said second material to about ninety seven parts HCFC-141*b*.

8. The method claim 7 wherein each of said dipping steps includes an allowing step wherein said needle is allowed a residence time in each of said solutions of said materials sufficient time sufficient for acquiring each of said coatings of said materials.

* * * * *